(12) United States Patent
Ramachandran et al.

(10) Patent No.: US 7,456,324 B2
(45) Date of Patent: Nov. 25, 2008

(54) METHODS FOR PREPARING HALOHYDRINS AND METHODS FOR PREPARING EPOXIDES

(75) Inventors: P. Veeraraghavan Ramachandran, West Lafayette, IN (US); Kamlesh J. Padiya, Maharashtra (IN); Venkatram R. Mereddy, Duluth, MN (US)

(73) Assignee: Great Lakes Chemical Corp., West Lafayette, IN (US)

( * ) Notice: Subject to any disclaimer, the term of this patent is extended or adjusted under 35 U.S.C. 154(b) by 110 days.

(21) Appl. No.: 11/809,821

(22) Filed: Jun. 1, 2007

(65) Prior Publication Data

US 2007/0282137 A1    Dec. 6, 2007

Related U.S. Application Data

(60) Provisional application No. 60/810,408, filed on Jun. 2, 2006.

(51) Int. Cl.
*C07C 29/09*    (2006.01)
*C07C 29/147*    (2006.01)

(52) U.S. Cl. ..................... 568/842; 568/841

(58) Field of Classification Search ............. 568/842, 568/841

See application file for complete search history.

(56) References Cited

U.S. PATENT DOCUMENTS

| 2,700,686 A | 1/1955 | Dickey et al. |
| 2,768,160 A | 10/1956 | Dickey et al. |

FOREIGN PATENT DOCUMENTS

WO    WO 91/09010    6/1991

*Primary Examiner*—Elvis O. Price
(74) *Attorney, Agent, or Firm*—Wells St. John P.S.

(57) ABSTRACT

The invention includes methods for preparing halohydrins and epoxides. A method of preparing halohydrins can include exposing $(R^1CHXCH_2O-)_2SO_2$ to $R^2COOH$ to produce $R^1CHXCH_2COOR^2$ and hydrolyzing the $R^1CHXCH_2COOR^2$ to produce the halohydrin $R^1CHXCH_2OH$. $R^1$ and $R^2$ can be the same or different single elements and/or organic groups and X can be a halogen. A method of preparing an epoxide can include combining a sulfuric acid containing solution with a halogen to produce a first mixture and exposing the first mixture to trifluoropropene to produce a second mixture. The second mixture can be combined with acetic acid to produce an acetyl halohydrin of trifluoropropene and the acetyl halohydrin can be hydrolyzed to form a halohydrin of trifluoropropene. The halohydrin can be converted to a trifluoropropyl epoxide.

49 Claims, 1 Drawing Sheet

A) 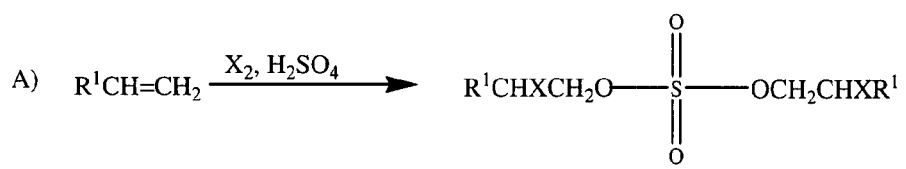
B) 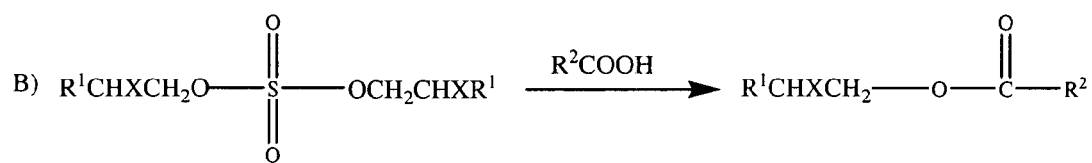
C) 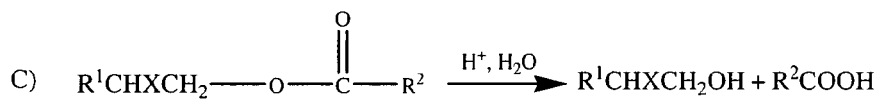
D) 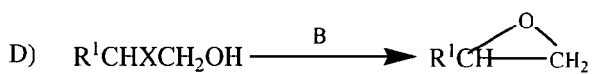

METHODS FOR PREPARING HALOHYDRINS AND METHODS FOR PREPARING EPOXIDES

RELATED PATENT DATA

This patent claims priority to U.S. provisional patent application 60/810,408, which was filed Jun. 2, 2006, entitled "Methods for Preparing Halohydrins and Methods for Preparing Epoxides" and which is incorporated by reference herein.

TECHNICAL FIELD

The present invention relates to methods for preparing halohydrins and methods for preparing epoxides.

BACKGROUND OF THE INVENTION

Polymers can be produced by polymerizing monomers having epoxide functionality. Monomers having epoxide functionality can be produced from monomers having halogenated carbons and hydroxyl groups situated adjacent the halogenated carbon. Compounds having this functionality are referred to as halohydrins. An exemplary halohydrin is $CF_3CHBrCH_2OH$.

Methods for preparing halohydrins and are provided.

SUMMARY OF THE INVENTION

The present invention provides methods for preparing halohydrins and epoxides. In one implementation, a method of preparing halohydrins includes exposing $(R^1CHXCH_2O-)_2SO_2$ to $R^2COOH$ to produce $R^2COOCH_2CHXR^1$ and hydrolyzing the $R^2COOCH_2CHXR^1$ to produce the halohydrin $R^1CHXCH_2OH$. $R^1$ and $R^2$ can be the same or different single elements and/or organic groups and X can be a halogen.

In one implementation, a method of preparing a halohydrin includes exposing a di(perhaloalkyl)haloethyl sulfate to a carboxylic acid compound to produce a (perhaloalkyl)haloethyl alkyl ester, and subsequently hydrolyzing the (perhaloalkyl)haloethyl alkyl ester to produce the halohydrin.

In one implementation, a method of preparing an epoxide includes combining a sulfuric acid containing solution with a halogen to produce a first mixture and exposing the first mixture to trifluoropropene (TFP) to produce a second mixture. The second mixture can be combined with acetic acid to produce an acetyl halohydrin of trifluoropropene and the acetyl halohydrin can be hydrolyzed to form a halohydrin of trifluoropropene. The halohydrin can be converted to a trifluoropropyl epoxide.

BRIEF DESCRIPTION OF THE DRAWINGS

Preferred embodiments of the invention are described below with reference to the following accompanying drawing.

The figure is an illustration of a synthetic scheme according to one aspect of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In one aspect the present invention includes methods for preparing halohydrins. Another aspect of the present invention includes methods for preparing epoxides. Various exemplary aspects of the present invention are described with reference to the figure. The figure depicts a synthetic scheme according to one aspect of the present invention for producing halohydrins and epoxides. In this exemplary depiction a four step synthetic scheme is illustrated (with the steps being A, B, C, and D, respectively). The present invention is not limited to this four step synthetic scheme. Persons having ordinary skill in the art will be able to modify and combine synthetic steps using the detailed description of the present invention.

Synthetic step A depicts the conversion of an olefin to a sulfate. The olefin can include compounds having the generic formula $R^1CH=CH_2$. $R^1$ can include organic groups such as $CF_3-$ or single elements such as H and/or halogens such as I, Br, Cl, or F. It has been generalized to include every possible olefin. $R^1$ can also include saturated and unsaturated carbon chains of organic compounds. An exemplary olefin for use in accordance with the present invention can be trifluoropropene $(CF_3CH=CH_2)$. The conversion of the olefin to the sulfate can include exposing the olefin to a halogen and sulfuric acid. The sulfuric acid can be in the form of a solution. An exemplary sulfuric acid containing solution can be oleum. Oleum can be a solution of $H_2SO_4$ that includes free $SO_3$ and up to as high as 80% (wt./wt.) free $SO_3$. The halogen can be provided in diatomic form, such as, for example, $I_2$, $Br_2$, or $Cl_2$.

The halogen and oleum can be in the form of a halogen-oleum mixture. The halogen-oleum mixture can be prepared by combining the halogen with oleum. The halogen-oleum mixture can include a $Br_2$-oleum mixture. The $Br_2$-oleum mixture can contain at least about 20% (wt./wt.) oleum. The oleum to bromine mole ratio of the $Br_2$-oleum mixture, in one aspect, can be at least 1:0.7, in another aspect, from about 1:0.7 to about 4:0.7 and, in a further aspect, can be about 2:0.8.

In an exemplary aspect, the olefin can be exposed to the halogen and oleum by bubbling the olefin in gas form into the halogen-oleum mixture. The olefin can also be exposed to the halogen-oleum mixture at a temperature from about 12° C. to about 22° C. The mole ratio of the olefin, the oleum, and the $Br_2$ during exposing, in one aspect, can be from about 1:1:0.7 to about 1:4:0.8 and in another aspect, at least about 1:2:0.8.

A sulfate can be produced upon exposure of the olefin to the halogen-oleum mixture. The sulfate can have the general formula $(R^1CHXCH_2O-)_2SO_2$. $(R^1CHXCH_2O-)_2SO_2$ can include di(perhaloalkyl)haloethyl sulfates and more particularly $(CF_3CHXCH_2O-)_2SO_2$ and even more particularly $(CF_3CHBrCH_2O-)_2SO_2$. In an exemplary aspect, $(CF_3CHBrCH_2O-)_2SO_2$ can be produced upon exposure of trifluoropropene to a $Br_2$-oleum mixture.

Referring next to scheme B of the figure, an acetyl halohydrin can be produced, in an exemplary aspect, upon exposure the sulfate to a carboxylic acid compound. The carboxylic acid compound generally has the formula $R^2COOH$. $R^2$ can include the functional group $CH_3-$, but may also include branched organic groups such as $(CH_3)_2CH-$. $R^2$ can also include single elements such as H and/or halogens such as I, Br, Cl, or F. $R^2$ can be the same or different from $R^1$. An exemplary carboxylic acid compound includes acetic acid.

The acetyl halohydrin can have the general formula $R^2COOCH_2CHXR^1$. $R^2COOCH_2CHXR^1$ also includes (perhaloalkyl)haloethyl alkyl esters. Exemplary acetyl halohydrins include $R^2COOOCH_2CHXR^1$, $CH_3COOCH_2CHXCF_3$, $CH_3COOCH_2CHXCF_3$ and more particularly $CH_3COOCH_2CHBrCF_3$. $R^2COOCH_2CHBrR^1$ can generally be referred to as an acetyl bromohydrin.

Referring next to scheme C of the figure, the acetyl halohydrin is hydrolyzed in one aspect to produce the halohydrin. In one implementation, the acetyl halohydrin can be hydrolyzed by exposing the acetyl halohydrin to a sulfuric acid solution. An exemplary sulfuric acid solution includes at least about 15% (wt./wt.) sulfuric acid. The halohydrin can have the general formula $R^1CHXCH_2OH$. $R^1CHXCH_2OH$ can include $CF_3CHXCH_2OH$ as well as $CF_3CHBrCH_2OH$. $R^1CHBrCH_2OH$ can generally be referred to as a bromohydrin.

Referring to scheme D of the figure, the halohydrin can be converted in one aspect to an epoxide in the presence of a base. In an exemplary aspect the halohydrin is exposed to a basic solution to produce the epoxide. The basic solution can comprise at least about 20% (wt./wt.) sodium hydroxide and/or from about 40% to about 70% sodium hydroxide as well as from about 50% to about 60% sodium hydroxide. The conversion of the halohydrin to the epoxide can also occur at a temperature of at least about 100° C. or from about 100° C. to about 130° C. The epoxide can have the general formula $R^1CHCH_2(O)$. $R^1CHCH_2(O)$ can also include $CF_3CHCH_2(O)$ and trifluoropropyl epoxide. In an exemplary embodiment (not shown) the epoxide may be utilized as a monomer in the production of polymers. An exemplary polymer can include fluoropolymers having at least one $CF_3$— group.

Aspects of the present invention will now be described with reference to the following non-limiting examples.

EXAMPLE 1

TABLE 1

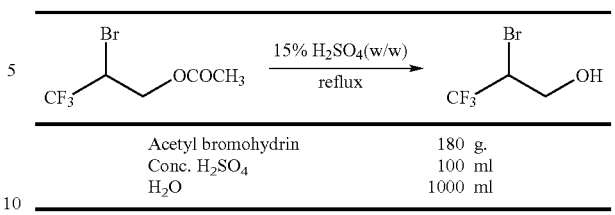

| | MW | mmoles | equivalents | Quantity |
|---|---|---|---|---|
| TFP | 96 | 0.186 | 1 | 18 g |
| Oleum | 20% | 0.375 | 2 | 150 g |
| Br$_2$ | 160 | 0.180 | 0.97 | 28.7 g |
| CH$_3$COOH | n/a | n/a | n/a | 300 ml |

In accordance with example 1, 150 g of oleum is taken in a 500 ml three-necked round-bottomed flask fitted with a dry ice condenser and a bubbler (TFP inlet tube) to which 28.7 g. $Br_2$ is then added to form a bromine-oleum mixture. The bromine-oleum mixture is stirred at room temperature for 3 hrs. The round-bottomed flask is covered with aluminum foil. TFP (18 g) is then bubbled through the mixture to form a reaction mixture. The rate of TFP addition is adjusted so that the temperature of the reaction mixture remains from about 12° C. to about 22° C. Upon addition of the TFP the bromine color is nearly gone, and the reaction mixture is stirred at room temperature for 1 hour. The reaction mixture is then poured into 300 ml of acetic acid taken in a 500 ml single-neck round-bottomed flask, stirred, and heated to 100° C. for 1 hr. This solution is cooled to room temperature and 100 ml of water is added and extracted four times with 100 ml portions of dichloromethane. (Dichloromethane forms an upper layer). Organic layers are combined and washed with saturated NaHCO$_3$ (4×200 ml), dried over anhydrous Na$_2$SO$_4$ (150 g.) and evaporated (without applying vacuum) to yield acetyl bromohydrin (43.9 g.) as a clear colorless liquid. Yield=43.9 g. (99.6%), $^1$H NMR: (CDCl$_3$, 300 MHz), δ ppm: 2.12(s, 3H), 4.34-4.56 (m, 3H)

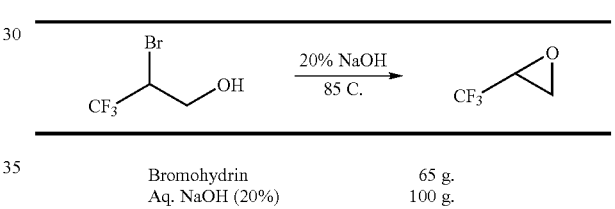

| Acetyl bromohydrin | 180 g. |
|---|---|
| Conc. H$_2$SO$_4$ | 100 ml |
| H$_2$O | 1000 ml |

In accordance with example 2, 1 L of water is placed in a 2 L single-necked round-bottomed flask fitted with a condenser. Concentrated H$_2$SO$_4$ (100 ml) is added slowly to the flask to produce a reaction mixture. Acetyl bromohydrin (180 g) is then added and the mixture is heated to reflux. The mixture is refluxed for 3 hrs until the mixture becomes homogeneous and further refluxed for 1 hour and then cooled to room temperature. The reaction mixture is saturated with NaCl and extracted with ether (200 ml×5). Combined ether layers are washed with saturated NaHCO$_3$, dried over anhydrous Na$_2$SO$_4$ and evaporated to yield bromohydrin 131 g. Yield=131 g. (89%) $^1$H NMR (CDCl$_3$, 300 MHz) δ ppm: 3.90-4.02 (m, 1H), 4.04-4.14 (m, 1H), 4.22-4.34 (m, 1H).

EXAMPLE 3

| Bromohydrin | 65 g. |
|---|---|
| Aq. NaOH (20%) | 100 g. |

In accordance with example 3, 65 g. bromohydrin is taken in a 300 ml three-necked round-bottomed flask fitted with a septum, a thermometer jacket, and a distillation set up. The bromohydrin is stirred and heated to 85° C. (oil bath temperature was 95° C.). NaOH (20% solution, 100 g) is introduced through septum by syringe. Product distills as NaOH is introduced. Yield=26 g. (69%) $^1$H NMR: (CDCl$_3$, 300 MHz) δ ppm: 2.90-2.94(m, 1H), 2.96-3.02(m, 1H), 3.38-3.46(m, 1H).

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of preparing halohydrins comprising exposing $(R^1CHXCH_2O—)_2SO_2$ to $R^2COOH$ to produce $R^2COOCH_2CHXR^1$ and hydrolyzing the $R^2COOCH_2CHXR^1$ to produce $R^1CHXCH_2OH$, $R^1$ and $R^2$ being a single element or an organic group, wherein $R^1$ and $R^2$ are the same or different and X is a halogen.

2. The method of claim 1 wherein the $(R^1CHXCH_2O—)_2SO_2$ comprises $(CF_3CHXCH_2O—)_2SO_2$, the $R^2COOH$ comprises acetic acid, the $R^2COOCH_2CHXR^1$ comprises $CH_3COOCH_2CHXCF_3$ and the $R^1CHXCH_2OH$ comprises $CF_3CHXCH_2OH$.

3. The method of claim 2 wherein the $(CF_3CHXCH_2O—)_2SO_2$ comprises $(CF_3CHBrCH_2O—)_2SO_2$, the $CH_3COOCH_2CHXCF_3$ comprises $CH_3COOCH_2CHBrCF_3$, and the $CF_3CHXCH_2OH$ comprises $CF_3CHBrCH_2OH$.

4. The method of claim 3 wherein the $(CF_3CHBrCH_2O—)_2SO_2$ is produced by exposing $CF_3CH=CH_2$ to $Br_2$ and sulfuric acid.

5. The method of claim 4 wherein the sulfuric acid is in the form of oleum.

6. The method of claim 5 wherein the exposing comprises combining the $CF_3CH=CH_2$, the oleum, and the $Br_2$ at a mole ratio of from about 1:1:0.7 to about 1:4:0.8.

7. The method of claim 5 wherein the exposing comprises combining the $CF_3CH=CH_2$, the oleum, and the $Br_2$ at a mole ratio of at least about 1:2:0.8.

8. The method of claim 5 wherein the $Br_2$ and oleum are in the form of a $Br_2$-oleum mixture.

9. The method of claim 8 wherein the $(CF_3CHBrCH_2O—)_2SO_2$ is produced by exposing $CF_3CH=CH_2$ to a $Br_2$-oleum mixture.

10. The method of claim 9 wherein the $Br_2$-oleum mixture is prepared from a 20% (wt./wt.) oleum solution.

11. The method of claim 9 wherein the exposing is performed at a temperature of from about 12° C. to about 22° C.

12. The method of claim 1 wherein $R^2COOH$ comprises acetic acid.

13. The method of claim 1 wherein X is I.

14. The method of claim 1 wherein X is Br.

15. The method of claim 1 wherein X is Cl.

16. The method of claim 1 wherein $R^1$ is $CF_3—$.

17. The method of claim 1 wherein $R^1$ is H.

18. The method of claim 1 wherein $R^1$ is F.

19. The method of claim 1 wherein $R^2$ is $CH_3—$.

20. The method of claim 1 wherein the hydrolyzing comprises exposing the $R^2COOCH_2CHXR^1$ to a sulfuric acid solution.

21. The method of claim 20 wherein the sulfuric acid solution comprises at least about 15% (wt./wt.) sulfuric acid.

22. The method of claim 1 further comprising converting the $R^1CHXCH_2OH$ to $R^1CHCH_2(O)$.

23. The method of claim 22 wherein the $R^1CHCH_2(O)$ comprises $CF_3CHCH_2(O)$.

24. The method of claim 22 wherein the converting comprises exposing the $R^1CHXCH_2OH$ to a basic solution.

25. The method of claim 24 wherein the basic solution comprises at least about 20% (wt./wt.) sodium hydroxide.

26. The method of claim 24 wherein the basic solution comprises from about 40% (wt./wt.) to about 70% (wt./wt.) sodium hydroxide.

27. The method of claim 24 wherein the basic solution comprises from about 50% (wt./wt.) to about 60% (wt./wt.) sodium hydroxide.

28. The method of claim 22 wherein the converting occurs at a temperature of at least about 100° C.

29. The method of claim 22 wherein the converting occurs at a temperature from about 100° C. to about 130° C.

30. A method of preparing a halohydrin comprising exposing a di(perhaloalkyl)haloethyl sulfate to a carboxylic acid compound to produce a (perhaloalkyl)haloethyl alkyl ester and hydrolyzing the (perhaloalkyl)haloethyl alkyl ester to produce the halohydrin.

31. The method of claim 30 wherein the di(perhaloalkyl)haloethyl sulfate comprises $(CF_3CHBrCH_2O—)_2SO_2$, the carboxylic acid compound comprises acetic acid, the (perhaloalkyl)haloethyl alkyl ester comprises $CH_3COOCH_2CHBrCF_3$ and the halohydrin comprises $CF_3CHBrCH_2OH$.

32. The method of claim 31 wherein the $(CF_3CHBrCH_2O—)_2SO_2$ is produced by exposing $CF_3CH=CH_2$ to $Br_2$ and sulfuric acid.

33. The method of claim 32 wherein the sulfuric acid is in the form of oleum.

34. The method of claim 33 wherein the exposing comprises combining the $CF_3CH=CH_2$, the oleum, and the $Br_2$ at a mole ratio of from about 1:1:0.7 to about 1:4:0.8.

35. The method of claim 33 wherein the exposing comprises combining the $CF_3CH=CH_2$, the oleum, and the $Br_2$ at a mole ratio of at least about 1:2:0.8.

36. The method of claim 33 wherein the $Br_2$ and the oleum are in the form of a $Br_2$-oleum mixture.

37. The method of claim 36 wherein the $Br_2$-oleum mixture is prepared from a 20% (wt./wt.) oleum solution.

38. The method of claim 37 wherein the exposing is performed at a temperature of from about 12° C. to about 22° C.

39. The method of claim 30 wherein the hydrolyzing comprises exposing the (perhaloalkyl)haloethyl alkyl ester to a sulfuric acid solution.

40. The method of claim 39 wherein the sulfuric acid solution comprises at least about 15% (wt./wt.) sulfuric acid.

41. The method of claim 30 further comprising converting the halohydrin to an epoxide.

42. The method of claim 41 wherein the epoxide comprises $CF_3CHCH_2(O)$.

43. The method of claim 41 wherein the converting comprises exposing the halohydrin to a basic solution.

44. The method of claim 43 wherein the basic solution comprises at least about 20% (wt./wt.) sodium hydroxide.

45. The method of claim 43 wherein the basic solution comprises from about 40% (wt./wt.) to about 70% (wt./wt.) sodium hydroxide.

46. The method of claim 43 wherein the basic solution comprises from about 50% (wt./wt.) to about 60% (wt./wt.) sodium hydroxide.

47. The method of claim 41 wherein the converting occurs at a temperature of at least about 100° C.

48. The method of claim 41 wherein the converting occurs at a temperature of from about 100° C. to about 130° C.

49. The method of claim 30 wherein the carboxylic acid compound comprises acetic acid.

* * * * *